United States Patent [19]
Walker, Jr. et al.

[11] Patent Number: 5,107,029
[45] Date of Patent: Apr. 21, 1992

[54] PROCESS FOR PREPARING DIKETONES AND KETO-ACIDS

[75] Inventors: Theodore R. Walker, Jr.; Winston J. Jackson, Jr.; Jean C. Fleischer, all of Kingsport, Tenn.

[73] Assignee: Eastman Kodak Company, Rochester, N.Y.

[21] Appl. No.: 556,678

[22] Filed: Jul. 23, 1990

[51] Int. Cl.$^5$ .............................................. C07C 45/46
[52] U.S. Cl. ...................... 568/319; 562/460; 568/42; 568/31; 568/316; 568/306; 558/415; 564/218; 564/430; 564/329
[58] Field of Search ............... 568/319, 322, 316, 31, 568/306, 42; 558/415; 564/218, 430, 329

[56] References Cited

U.S. PATENT DOCUMENTS

| | | | |
|---|---|---|---|
| 3,767,620 | 10/1973 | Angelo et al. | 260/47 |
| 4,453,010 | 6/1984 | Staniland | 508/319 |
| 4,611,033 | 9/1986 | Maresca | 525/419 |
| 4,816,556 | 3/1989 | Gay et al. | 528/176 |

FOREIGN PATENT DOCUMENTS

| | | | |
|---|---|---|---|
| 0075390 | 3/1983 | European Pat. Off. | 568/319 |
| 0128692 | 12/1984 | European Pat. Off. | 568/312 |
| 0262919 | 4/1988 | European Pat. Off. | 568/312 |
| 1378913 | 12/1974 | United Kingdom | 568/319 |
| 2116990 | 10/1983 | United Kingdom | 568/319 |

OTHER PUBLICATIONS

M. Ueda et al., *Makromol.*, 20, pp. 2675–2678 (1987).
M. Ueda et al., *Makromol. Chem., rapid Commun.*, 5, pp. 833–836 (1985).

*Primary Examiner*—James H. Reamer
*Attorney, Agent, or Firm*—Thomas R. Savitsky; Betty J. Deaton; William P. Heath, Jr.

[57] ABSTRACT

This invention concerns a process for preparing diketones and keto-acids by reacting a dicarboxylic acid and an aromatic compound in the presence of an alkylsulfonic acid such as methanesulfonic acid and an organic anhydride compound such as methanesulfonic anhydride or trifluoroacetic anhydride. The diketones and keto-acids can be used to prepare polyketones which are useful as molding plastics, coatings, films, fibers, and the like.

22 Claims, No Drawings

PROCESS FOR PREPARING DIKETONES AND KETO-ACIDS

FIELD OF INVENTION

This invention relates to a process for preparing diketones and keto-acids by reacting a dicarboxylic acid and an aromatic compound in the presence of an alkylsulfonic acid and an organic anhydride compound.

BACKGROUND OF THE INVENTION

In many prior art processes for preparing diketones, the diketones are minor by-products or the diketones are prepared by commercially impractical circuitous routes. Some diketones are reported to be prepared by well-known Friedel-Crafts reactions using diacid chlorides and such catalysts as $AlCl_3$. An example is contained in U.S. Pat. No. 4,816,556 which describes preparation of two diketones by reaction of 2 moles of diphenyl ether with 2 moles terephthalyl chloride (or 2 moles isophthalyl chloride) with 4 moles aluminum chloride as catalyst. Some disadvantages of this process are high cost which results from (1) the use of expensive diacid chlorides instead of diacids and (2) the use of large amounts of catalyst which is destroyed in the workup. Disposal of large amounts of aluminum wastes and corrosion from HCl by-product could also present problems Another prior art process discloses preparation of a diketone from isophthalic acid and anisole. This process is disclosed by Mitsuru Ueda and Masaki Sato, Makromol. 20, pp. 2675-2678 (1987). This diketone is not the type of this invention since it cannot be polymerized to give a polyketone. The reaction medium was PPMA, which is a mixture of phosphorus pentoxide and methanesulfonic acid, at a particular weight ratio. The phosphorus pentoxide acts as a dehydrator in that it takes up the water that is a product of the reaction and is itself converted to phosphorus acids. There are disadvantages to the use of phosphorus pentoxide in this reaction:

1. Handling. Ueda and Kano state that the phosphorus pentoxide "is difficult to handle because of its high reactivity toward moisture."

2. Recovery of dehydrator. The phosphorus acids are not practically recoverable for recycling. They are generally disposed of in an aqueous workup.

3. Cost. The inability to recycle phosphorus pentoxide makes a PPMA process more expensive than that of the present invention.

None of the above-described prior art discloses preparation of a keto-acid.

It would be highly desirable to have a process for preparing diketones and keto-acids that overcomes the problems of prior art processes.

SUMMARY OF THE INVENTION

The process of the present invention overcomes disadvantages of the prior art. The process of the present invention can be described as a process for producing a diketone or keto-acid compound comprising contacting
(A) an aliphatic dicarboxylic acid containing 3 to 20 carbon atoms, an aromatic dicarboxylic acid containing 8 to 30 carbon atoms, or a mixture thereof, with
(B) at least one polynuclear aromatic compound containing 10 to 30 carbon atoms,
in the presence of at least one solvent, at least one organic anhydride compound, and at least a catalytic amount of at least one alkylsulfonic acid containing 1 to 4 carbon atoms, under conditions to promote formation of the desired diketone or keto-acid compound.

A preferred process of the invention can be described as a process for producing a diketone or keto-acid compound comprising contacting
(A) at least one compound selected from the group consisting of terephthalic acid, chloroterephthalic acid, 5-methylisophthalic acid, isophthalic acid, 4,4'-biphenyldicarboxylic acid, 4,4'-stilbenedicarboxylic acid, 4,4'-oxydibenzoic acid, 1,3-naphthalenedicarboxylic acid, 1,5-naphthalenedicarboxylic acid, 1,6-naphthalenedicarboxylic acid, 1,7-naphthalenedicarboxylic acid, 2,5-naphthalenedicarboxylic acid, 2,6-naphthalenedicarboxylic acid, 2,7-naphthalenedicarboxylic acid, adipic acid, azelaic acid, sebacic acid, 1,3-cyclohexanedicarboxylic acid, and 1,4-cyclohexanedicarboxylic acid
with
(B) at least one compound selected from the group consisting of diphenyl ether, diphenyl sulfide, dibenzofuran, biphenyl, naphthalene, anthracene, fluorene, dibenzo-p-dioxin, xanthane, and phenanthrene
in the presence of at least one solvent and at least one organic anhydride compound selected from the group consisting of trifluoroacetic anhydride and methanesulfonic anhydride, and at least a catalytic amount of at least one alkylsulfonic acid containing one to four carbon atoms, at a temperature of about 0° to 100° C. for a time sufficient to form the desired diketone or keto-acid compound.

DETAILED DESCRIPTION OF THE INVENTION

The diketones and keto-acids produced according to this invention are useful as monomers for high heat- and chemical-resistant polyketones. These polyketones are useful as molding plastics, coatings, films, fibers, matrix resins, and the like. The diketone or keto-acid made by the process of the present invention is produced as HOH (i.e., water) is formed by the elimination of an OH group from a carboxylic acid and an H from hydrogen attached to an aromatic ring. Thus, in the case of diketone, the diacid becomes linked to two aromatic rings through its two carbonyl groups. In the case of ketoacid, the diacid becomes linked to one aromatic ring.

As is readily apparent, reactant (B) (that is, the aromatic compound) is not a dicarboxylic acid. Illustrative diketones and keto-acids produced by the process according to this invention include the following:

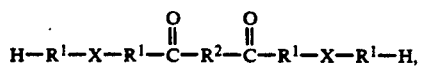

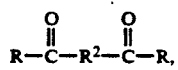

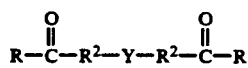

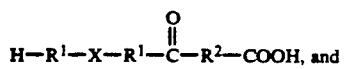

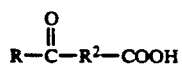

wherein each $R^1$ is, independently, (a) a phenylene moiety optionally substituted with up to three substituents selected from the group consisting of lower alkyl and lower alkoxy, (b) a naphthylene moiety optionally substituted with up to six substituents selected from the group consisting of lower alkyl and lower alkoxy, or (c) a biphenylene moiety optionally substituted with up to eight substituents selected from the group consisting of lower alkyl and lower alkoxy, each $R^2$ is, independently, $R^3$ or $R^4$, each $R^3$ is, independently, (a) a phenylene moiety optionally substituted with up to three substituents selected from the group consisting of lower alkyl, lower alkoxy, halo, hydroxy, acyl, perfluoroalkyl, cyano, nitro, dialkylamino, and acylamino, (b) a naphthalene moiety optionally substituted with up to six substituents selected from the group consisting of lower alkyl, lower alkoxy, halo, hydroxy, acyl, perfluoroalkyl, cyano, nitro, dialkylamino, and acylamino, or (c) a biphenylene moiety optionally substituted with up to eight substituents selected from the group consisting of lower alkyl, lower alkoxy, halo, hydroxy, acyl, perfluoroalkyl, cyano, nitro, dialkylamino, and acylamino, each $R^4$ is, independently, (a) a linear or branched aliphatic moiety containing 3 to 20 carbon atoms optionally substituted with up to 4 substituents selected from the group consisting of lower alkyl, lower alkoxy, halo, hydroxy, acyl, perfluoroalkyl, cyano, nitro, dialkylamino, and acylamino, or (b) a cycloaliphatic moiety containing 3 to 20 carbon atoms optionally substituted with up to 4 substituents selected from the group consisting of lower alkyl, lower alkoxy, halo, hydroxy, acyl, perfluoroalkyl, cyano, nitro, dialkylamino, and acylamino, X is a direct bond, O, S, or —CH=CH—;

Y is a direct bond, O, S,

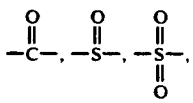

—CH=CH— or —O—$R^2$—O—; and

R is the residue of a polynuclear hydrocarbon after removal of a hydrogen atom and contains at least 10 carbon atoms (i.e., is a residue of reactant (B)).

As used herein the term "halo" refers to chloro, bromo, fluoro, or iodo; the term "lower alkyl" refers to alkyl groups having 1 to 10 carbon atoms; the term "lower alkoxy" refers to alkoxy groups having 1 to 10 carbon atoms; the term "acyl" refers to acyl groups having 1 to 10 carbon atoms; the term "perfluoroalkyl" refers to perfluoroalkyl groups having 1 to 10 carbon atoms; the term "dialkylamino" refers to dialkylamino groups wherein each alkyl group has 1 to 10 carbon atoms; and the term "acylamino" refers to acylamino groups having 1 to 10 carbon atoms. Preferred halo groups are iodo and fluoro; preferred lower alkyl groups are methyl, ethyl, propyl and isopropyl; preferred lower alkoxy groups are methoxy, ethoxy, propyloxy and 1-methylethoxy; preferred acyl groups have 1 to 4 carbon atoms; preferred perfluoroalkyl groups have 1 to 4 carbon atoms; preferred dialkylamino groups are wherein each alkyl moiety has 1 to 4 carbon atoms; and preferred acylamino groups have 1 to 4 carbon atoms. The optional substituents of the $R^1$, $R^2$, $R^3$ and $R^4$ groups may be the same or different.

The aromatic dicarboxylic acids (reactant (A)) which are useful in the process of the invention may contain 8 to 30 carbon atoms and include all of those disclosed in British Patent 2,166,990. Additionally, other aromatic dicarboxylic acids which are not disclosed in British Patent 2,166,990 are also useful in the process of the invention. Such dicarboxylic acids include those having the general formula HOOC—$R^3$—COOH, where —$R^3$— is as defined hereinabove and the —COOH moieties are directly bonded to an aromatic ring and are separated from each other by at least three carbon atoms. Other suitable dicarboxylic acids have the general formula HOOC—$R^3$—Y—$R^3$—COOH wherein —Y— and —$R^3$—, independently, are as defined hereinabove. It is preferred that the aromatic moiety or moieties are unsubstituted.

Examples of aromatic dicarboxylic acids which may be used as reactant (A) include the following:

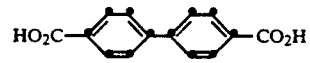

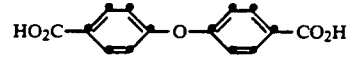

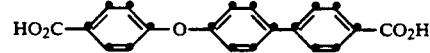

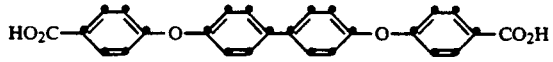

Preferred aromatic dicarboxylic acids include terephthalic acid, chloroterephthalic acid, 5-methylisophthalic acid, isophthalic acid, 4,4'-biphenyldicarboxylic acid, 4,4'-oxydibenzoic acid, 4,4'-stilbenedicarboxylic acid, 1,3-naphthalenedicarboxylic acid, 1,5-naphthalenedicarboxylic acid, 1,6-naphthalenedicarboxylic acid, 1,7-naphthalenedicarboxylic acid, 2,5-naphthalenedicarboxylic acid, 2,6-naphthalenedicarboxylic acid, and 2,7-naphthalenedicarboxylic acid.

For linear or branched aliphatic dicarboxylic acids useful as reactant (A), the carboxyl groups should be separated from each other by at least 2 carbon atoms. For cycloaliphatic dicarboxylic acids, the carboxyl groups should be attached directly to the ring and should be separated from each other by at least 3 carbon atoms. Typical aliphatic and cycloaliphatic dicarboxylic acids have the formula HOOC—$R^4$—COOH wherein $R^4$ is as defined hereinabove. Preferred $R^4$ moieties contain 1 to 6 carbon atoms and are unsubstituted. These aliphatic and cycloaliphatic dicarboxylic acids include adipic acid, azelaic acid, sebacic acid, 1,3-cyclohexanedicarboxylic acid (cis and/or trans isomers) and 1,4-cyclohexanedicarboxylic acid (cis and/or trans isomers).

The polynuclear aromatic compounds (reactant (B)) which may be used in the process of the invention may contain 10 to 30 carbon atoms and include all of those disclosed in British Patent 2,116,990 and U.S. Pat. No. 4,611,033, incorporated herein by reference, plus other compounds having the general formulae H—$R^1$—X—$R^1$—H or H—$R^5$—H, wherein each $R^1$, independently, and X are as defined hereinabove and $R^5$ is a polynuclear hydrocarbon moiety. Examples of $R^5$ moieties are those having 2, 3 or 4 fused rings, each of which is preferably aromatic, wherein the $R^5$ moiety is optionally substituted with up to 8 substituents such as with lower alkyl and/or lower alkoxy groups. Each of the fused rings of the $R^5$ moiety may also optionally contain 1, 2 or 3 hetero atoms such as O, N, S, and/or P. Preferred are unsubstituted, non-heterocyclic $R^5$ moieties wherein all rings are aromatic.

Examples of compounds which may be used as reactant (B) include the following:

cost. The alkylsulfonic acid is preferably substantially anhydrous, but small amounts of water can be tolerated. The alkylsulfonic acid acts as a catalyst for the reaction and is therefore present in at least a catalytic amount. However, it is also preferred that the alkylsulfonic acid perform a dual function and act as solvent, in whole or in part, for the process of the invention. The catalytic amount of alkylsulfonic acid is preferably at least about 20 mole % relative to reactant (A). A concentration of about 8 moles of alkylsulfonic acid per mole of desired product formed is preferred, but lesser or higher amounts may be used as dictated by the solubility of the acid and hydrocarbon starting materials and by the practicality of recovering the alkylsulfonic acid for recycle.

In some cases some of the alkylsulfonic acid may be replaced by excess aromatic compound to function as part of the solvent system, with the understanding that the aromatic compounds typically do not dissolve diac-

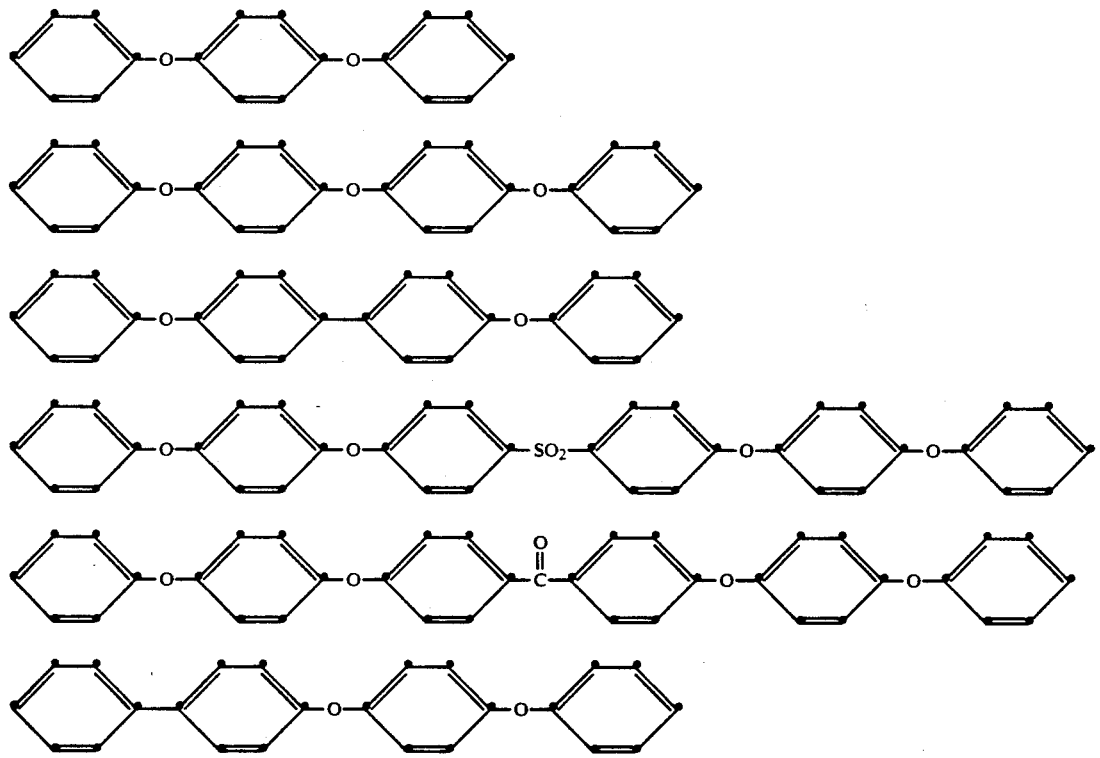

Other suitable compounds which may be used as reactant (B) include compounds such as diphenyl sulfide, fluorene, xanthene, dibenzofuran, thianthrene, phenoxathiin, dibenzo-p-dioxin, diphenylene, biphenyl, 4,4'-diphenoxybiphenyl, 2,2'-diphenoxybiphenyl, 1,2-diphenoxybenzene, 1,4-diphenoxybenzene, 1,3-diphenoxybenzene, 1-phenoxynaphthalene, 1,2-diphenoxynaphthalene, diphenyl ether, 1,5-diphenoxynaphthalene and the like.

Preferred aromatic compounds useful as reactant (B) are diphenyl ether, diphenyl sulfide, biphenyl, dibenzofuran, naphthalene, anthracene, phenanthrene, fluorene, xanthene, and dibenzo-p-dioxin.

The process of the invention is carried out in the presence of an alkylsulfonic acid(s) containing 1-4 carbon atoms and includes methanedisulfonic acid and 1,2-ethanedisulfonic acid. Methanesulfonic acid is preferred because of its commercial availability and its low ids as well as the sulfonic acids do. While some aromatic compounds are soluble in the sulfonic acids, most are not miscible. Therefore, if a large excess of aromatic compound is used, a two-phase system may result. In addition, part of the alkylsulfonic acid may be replaced by other solvents, especially well-known Friedel-Crafts solvents such as chlorinated hydrocarbons, o-dichlorobenzene, nitrobenzene, and nitromethane.

The process of the invention requires the presence of an organic anhydride. Although it is not desired to be bound to any particular theory or mechanism, it is believed that the organic anhydride acts as dehydrator to aid in producing an acylium ion from carboxylic acid and to remove the water produced in the reaction. The anhydride includes any organic anhydride that does not significantly react with the aromatic compound used in the reaction. Anhydrides containing electron-withdrawing groups are least likely to react with the aromatic compound, e.g., halogenated aliphatic carboxylic anhydrides, 2,4-dinitrobenzoic anhydride, p-(trimethylammonium)benzenesulfonic anhydride, and 1,2-ethanedisulfonic anhydride. The most preferred are trifluoroacetic anhydride and methanesulfonic anhydride because of availability, cost, and ease of recovery. Trifluoroacetic anhydride is useful particularly because, in the course of the reaction, it is converted to the low-boiling (bp=72° C.) trifluoroacetic acid which is easily recovered by distilling it from the reaction mixture.

Furthermore, trifluoroacetic acid is a good solvent for the other reagents and permits the use of less alkylsulfonic acid. Methanesulfonic anhydride is particularly useful when methanesulfonic acid is used as the solvent/catalyst because this anhydride is converted to methanesulfonic acid during the course of the reaction and does not require a separate recovery.

The amount of organic anhydride compound used in the process of the invention should be at least enough to react with all the water produced in the reaction, i.e., one mole anhydride for each carboxyl group of reactant (A), but excess organic anhydride may be used. The preferred amount of organic anhydride is about 2.1-2.8 moles anhydride per mole of diacid (reactant (A)).

The reaction may be carried out at 0° to 100° C., but temperatures up to 150° C. may be used with some reactants. The higher temperatures give faster reaction rates but also increase the probability of undesirable side reactions, particularly sulfone formation. At temperatures below 50° C. the reaction rates are appreciably slower. A temperature of about 60°-75° C. is preferred.

The time of the reaction may vary from a few minutes to several days, depending, for example, on the structure of the starting materials, the temperature, and the amount of anhydride and sulfonic acid. The optimum conditions for the preparation of the diketones by the process of the invention should be determined by routine experimentation for each. However, at 60°-75° C. most of the reactions are complete in at least about 2 hours, typically in 4-8 hours.

The diacid (reactant (A)), aromatic compound (reactant (B)), organic anhydride compound, and alkylsulfonic acid may be mixed in any order. Although excess aromatic hydrocarbon (reactant (B)) may be used in the process, it is not needed for avoidance of oligomer. The presence of oligomer does not interfere with polymerization as long as the amount of it is known so that polymerization may be conducted with the correct stoichiometry. However, reactant (B) may cause difficulties in isolation of the product. Since excess reactant (B) increases the rate of reaction, the preferred amount is a small stoichiometric excess of 5-10% relative to reactant (A), but the reaction can be conducted with no excess reactant (B).

The diketones and keto-acids prepared by the process of the invention may be isolated by precipitation in water followed by extraction with an alcohol. The water and alcohol typically remove >99% of the alkylsulfonic acid from the diketone or keto-acid. Residual sulfonic acid and any minor impurities may be removed by recrystallization of the diketone from a solvent. It is usually not necessary to remove small amounts of oligomer that form, since the oligomer will polymerize along with the diketone product to give the desired polyketone. Surprisingly, the highest purity is obtained when the diketone is purified by distillation. Considering the high boiling point of the diketones even under high vacuum (usually >300° C.), it would be expected that distillation would be accompanied by decomposition. However, the diketones exhibit unusual thermal stability.

The alkylsulfonic acid may be recovered for recycling by distilling the aqueous solution to separate water and the sulfonic acid.

In the course of a typical reaction most of the organic anhydride compound is converted to acid. Any remaining anhydride can be converted to acid during the aqueous workup. This acid can also be recovered for recycling by distillation of the aqueous filtrate. When a low-boiling anhydride (such as trifluoroacetic anhydride) is converted to a low-boiling acid (such as trifluoroacetic acid) during the reaction, the acid and any unreacted anhydride may be recovered by distilling directly from the reaction mixture before the aqueous workup. It should be understood that if the temperature is taken too high (e.g., about 100° C. or greater) during this distillation, the occurrence of an undesirable side reaction will probably become significant. This side reaction is the reaction of alkylsulfonic acid with diketone product and with aromatic compound to produce sulfones.

The diketone formed by the process of the invention is typically formed with production of only small amounts of oligomer. It is not desired to be bound by any particular theory or mechanism; however, it is believed that when a carbonyl of the diacid is attached to one ring of the aromatic compound, the other ring(s) of the aromatic compound is then sufficiently deactivated to inhibit reaction with a carboxyl group.

The diketone may then be converted to a polyketone under more reactive conditions. For example, one gram-mole of diketone and one gram-mole of a diacid chloride in a reaction catalyzed by AlCl$_3$ in a dichlorobenzene solvent will produce a polyketone. Unstable cyclic alcohol end-groups, such as described in U.S. Pat. No. 3,767,620, cannot occur. In the diketone structure as follows:

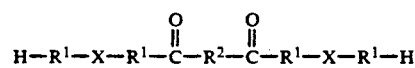

only the terminal aromatic rings can react with the acid chloride. The internal rings are deactivated by the carbonyls. If the acid chloride reacts at the ortho position of a terminal aromatic ring, it cannot further react with the nearby (but deactivated) internal ring to produce thermally-unstable cyclic alcohol, such as is described in U.S. Pat. No. 3,767,620. In addition, if a dicarboxylic acid component different from that used in making the diketone is used for preparing the polyketone, a uniform alternating structure can be produced.

Keto-acid may also be polymerized to polyketone under more reactive conditions, such as a reaction medium of triflic acid/phosphorus pentoxide, or the keto-acid may be converted to keto-acid chloride and polymerized with well-known Friedel-Crafts catalysts such as AlCl$_3$ Unstable cyclic alcohol cannot be produced during the polymerization for the same reason that it could not be produced when diketone was polymerized. The keto-acid, like diketone, had been purified to remove all non-para isomers. Ortho isomers can cyclize, para cannot.

A keto-acid is stoichiometrically correct. It does not require the addition of another monomer for polymerization. However, copolymers may be produced by polymerizing two or more keto-acids or by polymerizing a keto-acid, a diketone, and enough diacid to balance the stoichiometry.

In the reaction of an aromatic hydrocarbon with a diacid to produce diketone, it is not necessary that the reaction go to completion. A mixture of diacid, keto-acid, and diketone is suitable for polymerization. It is only necessary that enough aromatic hydrocarbon is reacted to produce ketone, so that more aromatic compound will not need to be added during the polymerization. To get the proper stoichiometry, diacid (which may or may not be the same diacid) is added but not aromatic hydrocarbon. The reason for not adding aromatic hydrocarbon to the polymerization mixture is that ketone isomers can occur which may cyclize to form unstable units. For example,

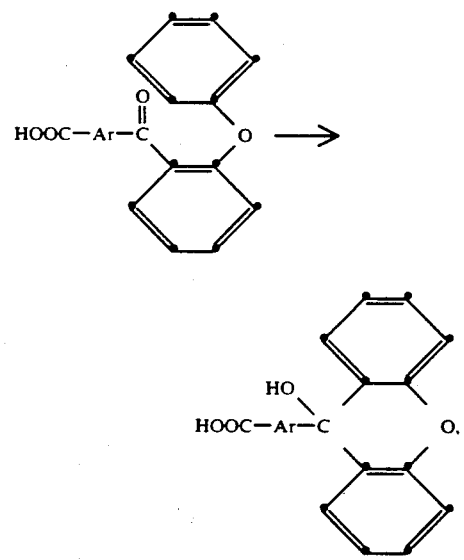

wherein PH is phenyl and Ar is an aromatic moiety.

When diketones or keto-acids are made, such "ortho" isomers that may cyclize are typically removed during purification. During polymerization "ortho" substitution can occur but cyclization cannot because the adjacent ring has been deactivated by a carbonyl.

Before polymerizing a product mixture of diacid, keto-acid, and diketone, the exact amount of each component should be determined. A convenient method of doing this is high-pressure liquid chromatography (HPLC), which gives an accurate weight % of each component.

The following examples are submitted for a better understanding of the invention, but should not be construed as a limitation thereon. In the examples the reactions were followed by field desorption mass spectrometry (FDMS) to determine when the reactions were complete.

Product identifications are made by FDMS, nuclear magnetic resonance (NMR), and high pressure liquid chromatography (HPLC).

EXAMPLE 1

To a 3-L reaction flask is added with stirring 192 g (2.0 moles) methanesulfonic acid, 408 g (2.4 moles) diphenyl ether, 166 g (1.0 mole) isophthalic acid, and 484 g (2.3 moles) trifluoroacetic anhydride.

The mixture is heated with stirring at 67°-70° C. for 5 hours and is then allowed to cool. Trifluoroacetic acid and remaining anhydride is removed by distillation at 6-8 mm Hg. After cooling the reaction mixture to 30°-35° C., 750 mL water is added dropwise to the rapidly stirring mixture. Filtration gives a granular solid which is washed with 500 mL water. After air-drying it weighed 545 g.

A mixture of the solid and 1250 mL methanol is refluxed for about 1 hour and allowed to cool. The solid is collected and washed with 300 mL of methanol to give 448 g (95% yield) of product. FDMS and liquid chromatography show the product to be 1,3-bis(4-phenoxybenzoyl)benzene containing 7% tetraketone oligomer.

EXAMPLE 2

This example illustrates the use of methanesulfonic anhydride as dehydrator/promoter.

To a 300 mL reaction flask is added with stirring 38.4 g (0.4 mole) methanesulfonic acid, 20.4 g (0.12 mole) diphenyl ether, 8.3 g (0.05 mole) isophthalic acid, and 25 g (0.14 mole) methanesulfonic anhydride.

The mixture is heated with stirring at 68°-71° C. for 5.5 hours. Samples of reaction mixture are taken during the reaction period and precipitated in water. FDMS analysis of the samples shows that the reaction is complete between 1.5 and 3.5 hours reaction time. The reaction mixture is poured into about 1 L water. The supernatant aqueous layer is decanted from the semisolid product which is washed with more water and again separated by decantation. Isopropyl alcohol, 150 mL, is added to the product and the mixture is heated on a steam bath several hours.

The product does not entirely dissolve. After cooling overnight to room temperature, the product is collected and washed with cool methanol to give 20.2 g (86% yield) of 1,3-bis(4-phenoxybenzoyl)benzene containing 8% of the tetraketone oligomer described in Example 1.

EXAMPLE 3

This example illustrates the use of trichloroacetic anhydride as dehydrator/promotor.

A mixture of 38.4 g (0.4 mole) methanesulfonic acid, 20.4 g (0.12 mole) diphenyl ether, 8.3 g (0.05 mole) isophthalic acid, and 37.0 g (0.12 mole) trichloroacetic anhydride is heated 4 hours at 65°-70° C. with stirring.

The reaction mixture is poured into ~250 mL of stirring cold water. After decanting the supernatent liquid, the product is triturated in 50 mL isopropyl alcohol with heating on a steam bath. The mixture is cooled, filtered, and the solid product washed with methanol to give 21.7 g (92% yield) of 1,3-bis(4-phenoxybenzoyl)benzene containing some tetraketone oligomer.

EXAMPLE 4

This example illustrates the use of biphenyl as the aromatic component.

A mixture of 76.8 g (0.8 mole) methanesulfonic acid, 63 g (0.3 mole) trifluoroacetic anhydride, 16.6 g (0.1 mole) isophthalic acid, and 33.9 g (0.22 mole) biphenyl in a 500-mL reaction flask is heated at 68°-70° C. for 7.5 hours. The reaction mixture is poured into 400 mL ice water. The supernatent liquid is decanted from the solid product which is then crushed and slurried with more cold water. The solid is collected and dried to give 47.4 g.

The product is further purified by recrystallization from 300 mL N,N-dimethylformamide to give 23.5 g (53.7% yield) of 1,3-bis(4-phenylbenzoyl)benzene. Mp 182°-186° C.

EXAMPLE 5

This example illustrates the use of 2,6-naphthalenedicarboxylic acid as the diacid component.

A mixture of 76.8 g (0.8 mole) methanesulfonic acid, 63 g (0.3 mole) trifluoroacetic anhydride, 21.6 g (0.1 mole) 2,6-naphthalenedicarboxylic acid, and 40.8 g (0.24 mole) diphenyl ether in a 500-mL reaction flask is heated with stirring at 68°-70° C. for 7 hours. FDMS analysis of the reaction mixture shows that the major product is 2,6-bis(4.phenoxybenzoyl)naphthalene.

EXAMPLE 6

This example illustrates the use of a diacid with very poor solubility (<5%) in methanesulfonic acid.

A mixture of 96 g (1.0 mole) methanesulfonic acid, 42 g (0.2 mole) trifluoroacetic anhydride, 8.3 g (0.05 mole) terephthalic acid, and 19.5 g (0.115 mole) diphenyl ether is heated at 80°-85° C. for 1 hour. Unreacted terephthalic acid is collected by filtration; about 50% had reacted. The filtrate is diluted with a large amount of water to precipitate all water insolubles, which are collected by filtration and washed with water and hexane. FDMS and liquid chromatography analyses show that the product is the diketone, 1,4-bis(4-phenoxybenzoyl)benzene, containing small amounts of tetraketone oligomer and methyl sulfones. No significant amount of terephthalic acid or keto-acid are present.

EXAMPLE 7

This example illustrates the purification of a diketone product by distillation.

1,3-Bis(4-phenoxybenzoyl)benzene, 201 g, is placed in a distilling flask equipped with thermometer well and capillary ebulator.

The diketone is distilled through a 3-in. unpacked column and into a round-bottom receiver that is cooled with dry ice. A vacuum line is attached to the receiver. No condenser is used above the column.

A 16.5 g forecut is taken at 311°-321° C. (head temperature) and 0.3 mm Hg pressure. The main cut is collected at 324°-328° C. and 0.3 mm Hg to give high purity diketone. During the collection of the main cut, the base temperature is 343°-363° C., and there is no evidence of decomposition. The yield on this distillation is 80%.

Another sample of the same diketone is stripped of low boilers (including diphenyl ether) by heating at 300° C. under 1 mm Hg pressure. A short Vigreux column is used. Afterwards the sample is distilled in a 5-in. molecular still at 240° C. and 10 microns pressure.

The invention has been described in detail with particular reference to preferred embodiments thereof, but it will be understood that variations and modifications can be effected within the spirit and scope of the invention.

We claim:

1. A process for producing a diketone or keto-acid compound comprising
    contacting
    (A) an aliphatic dicarboxylic acid containing 3 to 20 carbon atoms, an aromatic dicarboxylic acid containing 8 to 30 carbon atoms, or a mixture thereof, with
    (B) at least one polynuclear aromatic compound containing 10 to 30 carbon atoms, having the following formula:

$$H-R^1-X-R^1-H$$

wherein
    each $R^1$ is, independently,
    (a) a phenylene moiety optionally substituted with up to three substituents selected from the group consisting of lower alkyl and lower alkoxy,
    (b) a naphthylene moiety optionally substituted with up to six substituents selected from the group consisting of lower alkyl and lower alkoxy, or
    (c) a biphenylene moiety optionally substituted with up to eight substituents selected from the group consisting of lower alkyl and lower alkoxy; $\propto X$ is a direct bond, O, S, or $-CH=CH-$; or
    a compound of the formula $$H-R^5-H$$

wherein $R^5$ is a polynuclear hydrocarbon moiety. in the presence of at least one solvent, at least one of either an alkylsulfonic anhydride containing one to four carbon atoms or a halogenated acetic anhydride compound, and at least a catalytic amount of at least one alkylsulfonic acid containing 1 to 4 carbon atoms, under conditions to promote formation of the desired diketone or keto-acid compound.

2. The process of claim 1 wherein reactant (A) is
    (I) a compound of the formula $$HOOC-R^3-COOH$$

wherein $R^3$ is
    (a) a phenylene moiety optionally substituted with up to three substituents selected from the group consisting of lower alkyl, perfluoroalkyl, lower alkoxy, halo, hydroxy, acyl, cyano, nitro, dialkylamino, and acylamino,
    (b) a naphthylene moiety optionally substituted with up to six substituents selected from the group consisting of lower alkyl, perfluoroalkyl, lower alkoxy, halo, hydroxy, acyl, cyano, nitro, dialkylamino, and acylamino, or
    (c) a biphenylene moiety optionally substituted with up to eight substituents selected from the group consisting of lower alkyl, perfluoroalkyl, lower alkoxy, halo, hydroxy, acyl, cyano, nitro, dialkylamino, and acylamino,
    and wherein the —COOH moieties are directly bonded to an aromatic ring and are separated from each other by at least three carbon atoms;
    (II) a compound of the formula $$HOOC-R^3-Y-R^3-COOH$$

wherein Y is a direct bond, —O—, —S—,

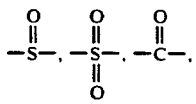

—CH=CH— or —O—R³—O—, and each R³, independently, is as defined hereinabove;

(III) a linear or branched aliphatic dicarboxylic acid optionally substituted with up to 4 substituents selected from the group consisting of lower alkyl, perfluoroalkyl, lower alkoxy, halo, hydroxy, acyl, cyano, nitro, dialkylamino, and acylamino, wherein the two carboxyl moieties are separated from each other by at least two carbon atoms; or (IV) cycloaliphatic dicarboxylic acid optionally substituted with up to 4 substituents selected from the group consisting of lower alkyl, perfluoroalkyl, lower alkoxy, halo, hydroxy, acyl, cyano, nitro, dialkylamino, and acylamino, wherein the two carboxyl groups are attached directly to the cycloaliphatic ring and are separated from each other by at least three carbon atoms.

3. The process of claim 1 wherein reactant (A) is selected from the group consisting of terephthalic acid, chloroterephthalic acid, 5-methylisophthalic acid, isophthalic acid, 4,4'-biphenyldicarboxylic acid, 4,4'-stilbenedicarboxylic acid, 4,4'-oxydibenzoic acid, 1,3-naphthalenedicarboxylic acid, 1,5-naphthalenedicarboxylic acid, 1,6-naphthalenedicarboxylic acid, 1,7-naphthalenedicarboxylic acid, 2,5-naphthalenedicarboxylic acid, 2,6-naphthalenedicarboxylic acid, 2,7-naphthalenedicarboxylic acid, adipic acid, azelaic acid, sebacic acid, 1,3-cyclohexanedicarboxylic acid, and 1,4-cyclohexanedicarboxylic acid.

4. The process of claim 1 wherein reactant (B) is selected from the group consisting of diphenyl ether, diphenyl sulfide, biphenyl, naphthalene, anthracene, dibenzofuran, fluorene, xanthane, phenanthrene, and dibenzo-p-dioxin.

5. The process of claim 1 wherein a diketone compound is produced which is followed by the additional step of reacting the diketone with a diacid halide under conditions that promote formation of a polyketone.

6. The process of claim 1 wherein said alkylsulfonic acid is methanesulfonic acid.

7. The process of claim 1 wherein said alkylsulfonic acid catalyst also is the solvent.

8. The process of claim 7 wherein reactant (B) functions as a portion of the solvent.

9. The process of claim 1 wherein said organic anhydride compound is methanesulfonic anhydride or trifluoroacetic anhydride.

10. The process of claim 1 wherein said organic anhydride compound is the anhydride of said alkyl sulfonic acid.

11. The process of claim 1 carried out at a temperature of about 0° to 165° C.

12. The process of claim 1 carried out at a temperature of about 60° to 75° C.

13. The process of claim 1 wherein there is about a 5 to 10% stoichiometric excess of reactant (B) relative to reactant (A).

14. The process of claim 1 wherein the catalytic amount of alkylsulfonic acid is at least about 20 mole % of reactant (A).

15. The process of claim 1 wherein the amount of organic anhydride compound is about 2.1 to 2.8 moles of organic anhydride compound per mole of reactant (A).

16. The process of claim 1 having a reaction time of at least about 2 hours.

17. The process of claim 1 including the additional step of purifying said diketone or keto-acid compound.

18. The process of claim 17 wherein the purifying step is carried out by recrystallization, distillation or a mixture thereof.

19. The process of claim 18 including the additional steps of recovering and recycling any remaining alkylsulfonic acid, organic anhydride compound, or mixture thereof.

20. A process for producing a diketone or keto-acid compound comprising
contacting
(A) at least one compound selected from the group consisting of terephthalic acid, chloroterephthalic acid, 5-methylisophthalic acid, isophthalic acid, 4,4'-biphenyldicarboxylic acid, 4,4'-stilbenedicarboxylic acid, 4,4'-oxydibenzoic acid, 1,3.naphthalenedicarboxylic acid, 1,5-naphthalenedicarboxylic acid, 1,6-naphthalenedicarboxylic acid, 1,7-naphthalenedicarboxylic acid, 2,5-naphthalenedicarboxylic acid, 2,6-naphthalenedicarboxylic acid, 2,7-naphthalenedicarboxylic acid, adipic acid, azelaic acid, sebacic acid, 1,3-cyclohexanedicarboxylic acid, and 1,4-cyclohexanedicarboxylic acid
with
(B) at least one compound selected from the group consisting of diphenyl ether, diphenyl sulfide, biphenyl, naphthalene, anthracene, dibenzofuran, fluorene, xanthane, phenanthrene, and dibenzo-p-dioxin
in the presence of at least one solvent and at least one organic anhydride compound selected from the group consisting of trifluoroacetic anhydride and methanesulfonic anhydride, and at least a catalytic amount of at least one alkylsulfonic acid containing one to four carbon atoms,
at a temperature of about 0° to 100° C. for a time sufficient to form the desired diketone or keto-acid compound.

21. The process of claim 20 wherein both the solvent and alkylsulfonic acid are methanesulfonic acid.

22. The process of claim 21 wherein the amount of reactant (B) is about a 5 to 10% stoichiometric excess relative to reactant (A), the amount of organic anhydride compound is about 2.1 to 2.8 moles of organic anhydride compound per mole of reactant (A), and wherein said process is carried out at about 60° to 70° C. for at least about 2 hours.

* * * * *